US00PP22296P2

(12) United States Plant Patent
Jablonski

(10) Patent No.: US PP22,296 P2
(45) Date of Patent: Dec. 6, 2011

(54) ***THUJA* PLANT NAMED 'JANTAR'**

(50) Latin Name: *Thuja occidentalis*
Varietal Denomination: Jantar

(75) Inventor: Jacub Jablonski, Torun (PL)

(73) Assignees: Jacub Jablonski, Torún (PL); Cornelius Petrus Franciscus Kools, Deurne (NL); Franciscus Van Gils, Hulsel (NL); Wlodzimierz Flejszer, Skierniewice (PL); Nemezjusz Piotr Nowaczyk, Kobylin (PL)

( * ) Notice: Subject to any disclaimer, the term of this patent is extended or adjusted under 35 U.S.C. 154(b) by 1 day.

(21) Appl. No.: 12/803,272

(22) Filed: Jun. 23, 2010

(51) Int. Cl.
*A01H 7/00* (2006.01)

(52) U.S. Cl. ..... Plt./213

(58) Field of Classification Search ..... Plt./213
See application file for complete search history.

*Primary Examiner* — Susan McCormick Ewoldt
(74) *Attorney, Agent, or Firm* — Jondle & Associates, P.C.

(57) ABSTRACT

'Jantar' is a new *Thuja* variety particularly distinguished by being a medium-sized evergreen shrub, having a medium growth rate, an upright narrow, pyramidal plant habit with pointed tip, dense foliage with leaves held tightly, trunk and twigs completely hidden, and bright amber-yellow to medium-yellow foliage is disclosed.

2 Drawing Sheets

Genus and species: *Thuja occidentalis.*
Variety denomination: 'Jantar'.

BACKGROUND OF THE NEW PLANT

The present invention relates to a new and distinct variety of *Thuja* plant botanically known as *Thuja occidentalis* and hereinafter referred to by the variety name 'Jantar'. The new *Thuja* is a naturally-occurring branch mutation of a selection of *Thuja occidentalis* 'Emerald Green', also known as 'Smaragd' (unpatented). 'Jantar' was discovered and selected in Lysomice, Poland in 2000 and is characterized by its bright amber-yellow to medium-yellow foliage and upright narrow, pyramidal growth habit.

Asexual reproduction of the new *Thuja* by softwood cuttings in a controlled environment in Lysomice, Poland and Deurne, The Netherlands since 2006 has shown that the unique features of 'Jantar' are stable and reproduce true to type in successive generations via softwood cuttings.

SUMMARY OF THE INVENTION

The following characteristics of the new variety have been repeatedly observed and can be used to distinguish 'Jantar' as a new and distinct variety of *Thuja* plant:

1. Medium-sized evergreen shrub;
2. Medium growth rate;
3. Upright narrow, pyramidal habit with pointed tip;
4. Dense foliage with leaves held tightly, trunk and twigs completely hidden; and
5. Bright amber-yellow to medium-yellow foliage.

DESCRIPTION OF THE PHOTOGRAPHS

This new *Thuja* plant is illustrated by the accompanying photographs which show the plant form and foliage. The colors shown are as true as can be reasonably obtained by conventional photographic procedures. Photographs were taken of a 5-year-old plant in May 2009.

Figure 1:
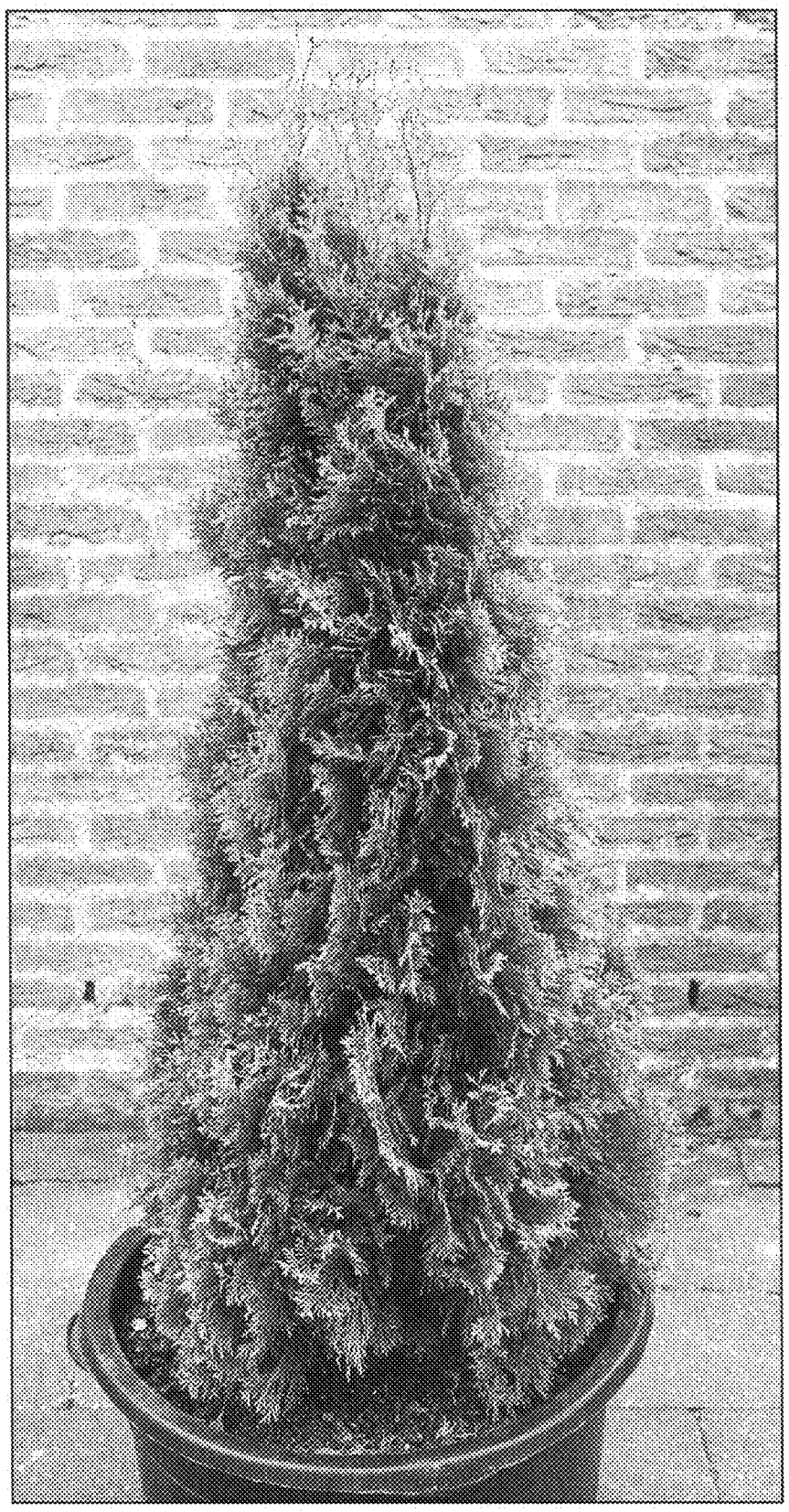
Figure 2:
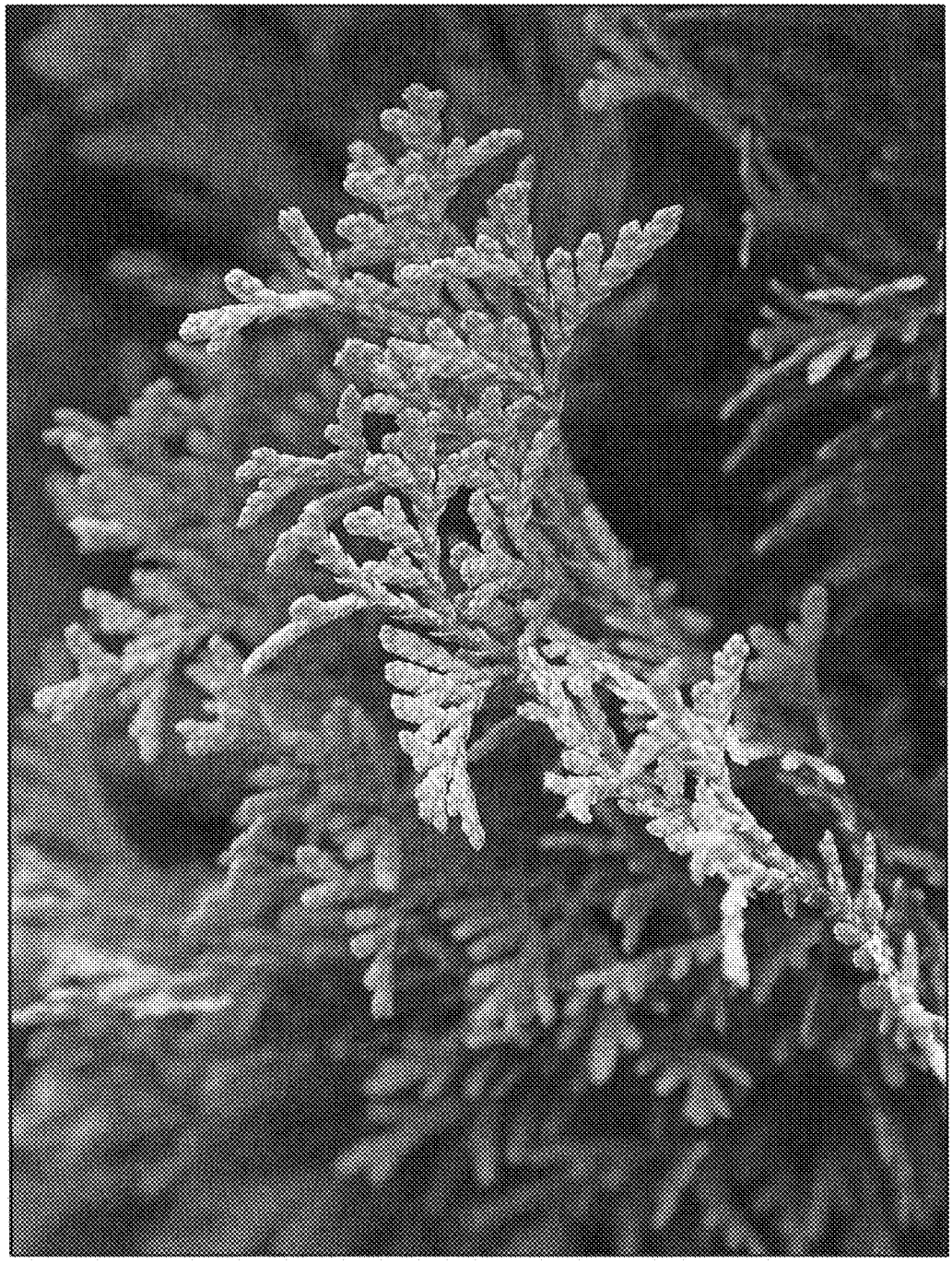

FIG. 1 shows the overall plant habit.
FIG. 2 shows a close-up of the leaves.

DESCRIPTION OF THE NEW VARIETY

The following detailed description sets forth the distinctive characteristics of 'Jantar'. The data which define these characteristics were collected from asexual reproductions carried out in Deurne, The Netherlands in May 2009. The detailed description was taken from 6-year old plants grown outdoors under normal outdoor light from transplanting of rooted cuttings into 3-gallon containers. No growth retardants were used.

DETAILED BOTANICAL DESCRIPTION OF THE NEW VARIETY

Classification:
- *Family.*—Cupressaceae.
- *Species.—Thuja occidentalis* 'Jantar'.
- *Common name.*—Arborvitae, American Arborvitae, Northern Whitecedar.

Parentage:
- *Parent.*—Naturally-occurring branch mutation of *Thuja occidentalis* 'Emerald Green', also known as 'Smaragd' (unpatented).

Plant:
- *Type.*—Perennial, shrub, conifer.
- *Propagation type.*—Softwood.
- *Shape.*—Narrow pyramidal.
- *Growth habit.*—Upright.
- *Growth rate.*—Average, 10.0 cm per season, stronger as a young plant.
- *Time to initiate roots during the summer.*—60 days.
- *Number of days to produce a rooted young plant during the summer.*—150 days.
- *Number of days to initiate roots during the winter with an average air temperature of* 6° *C. to* 15° *C..*—200 days.

*Time to a finished plant.*—24 months.

*Roots.*—Density: Moderate. Branching: Moderate. Color: Light grayish brown. Thickness: Medium. Texture: Moderately fleshy.

*Use.*—*Thuja occidentalis* is a slow growing coniferous shrub that can be used as a solitary garden plant or grouped as a hedge planting.

*Size.*—Height: 131.0 cm. Width (spread): 53.5 cm.

*Vigor.*—Moderate to high.

Lateral branches:

*Branching habit.*—Main stem grows from base and has lateral branches.

*Number of lateral branches per plant* (*average*).—144.

*Appearance of lateral branches.*—Rounded, covered with scale-like leaves.

*Color.*—Young branch: One-year-old stems are between RHS 144A (Yellow-green) and RHS 151A (Yellow-green). Mature branch: Second-year-old bark is RHS N199A (Grey-brown) and RHS N199B (Grey-brown); older bark is RHS 178A (Greyed-red).

*Diameter* (*average*).—0.33 cm.

*Length* (*average*).—25.0 cm.

*Length of internode* (*average*).—1.6 cm.

*Texture.*—Dull, smooth.

*Strength.*—Strong.

*Pubescence.*—Absent.

Leaves:

*General description.*—Arrangement: Opposite and simple. Fragrance: When crushed, small glands on the scales emit a strong scent typical of species; Shape: Elliptic; Length (average): 0.1 cm; Width (average): 0.075 cm; Color: RHS 144C (Yellow-green) and RHS 144D (Yellow-green).

*Aspect* (*arrangement on stem*).—Rounded, covered with scale-like leaves.

*Shape.*—Ovate, scale-like.

*Apex.*—Apiculate.

*Base.*—Cuneate.

*Margin.*—Entire.

*Attachment.*—Sessile (no petioles).

*Appearance.*—Smooth, glossy.

*Mature leaf length* (*average*).—0.3 cm.

*Mature leaf width* (*average*).—0.1 cm.

*Quantity per lateral branch* (*average*).—2400.

*Pubescence.*—Absent.

*Durability to stresses.*—Very high.

*Venation.*—Veins not visible.

*Color.*—Young foliage (both surfaces): Outer tips are RHS 163A (Greyed-orange) and RHS 163B (Greyed-orange); later turning to RHS 151A (Yellow-green) and RHS 151B (Yellow-green). Mature foliage (both surfaces): From RHS 143B (Green) to RHS 144A (Yellow-green).

Cone and seed production: No fruits or seeds detected to date.

Disease and insect resistance: No unique or distinguishing resistance or susceptibility to common *Thuja* pathogens or pests observed.

Weather tolerance: Plants of the new *Thuja* have been observed to be very winter hardy and to have great sun tolerance. They have also been observed to tolerate low temperatures to about −17° C. and high temperatures to about 35° C.

COMPARISON WITH PARENT VARIETY

'Jantar' is a new and distinct variety of *Thuja* having dense bright amber-yellow to medium-yellow foliage and an upright narrow, pyramidal growth habit with a pointed tip. 'Jantar' is most similar to its parent 'Emerald Green' (unpatented), however there are differences. 'Jantar' has dense bright amber-yellow to medium-yellow foliage, while 'Emerald Green' has moderately dense green foliage.

COMPARISON WITH KNOWN VARIETIES

'Jantar' differs from the commercial *Thuja* variety 'Yellow Ribbon' (unpatented) in that 'Jantar' has dense bright amber-yellow to medium-yellow foliage, while 'Yellow Ribbon' has moderately dense golden-yellow foliage.

'Jantar' differs from the commercial *Thuja* variety 'Mirjam' (U.S. Plant Pat. No. 20,127) in that 'Jantar' has an average of 144 lateral branches per plant, while 'Mirjam' has approximately 42 lateral branches per plant.

I claim:

1. A new and distinct variety of *Thuja* plant as shown and described herein.

* * * * *